(12) United States Patent
Hamilton

(10) Patent No.: US 10,134,490 B2
(45) Date of Patent: Nov. 20, 2018

(54) METHOD AND SYSTEM FOR MONITORING LABOUR PROGRESSION FOR AN OBSTETRICS PATIENT

(75) Inventor: Emily Hamilton, Verdun (CA)

(73) Assignee: PERIGEN, INC., Cary, NC (US)

( * ) Notice: Subject to any disclaimer, the term of this patent is extended or adjusted under 35 U.S.C. 154(b) by 1431 days.

(21) Appl. No.: 11/416,281

(22) Filed: May 1, 2006

(65) Prior Publication Data

US 2007/0255588 A1    Nov. 1, 2007

(51) Int. Cl.
*G16H 15/00* (2018.01)
*G16H 10/00* (2018.01)
(Continued)

(52) U.S. Cl.
CPC ........... *G16H 40/63* (2018.01); *A61B 5/0011* (2013.01); *A61B 5/02411* (2013.01);
(Continued)

(58) Field of Classification Search
CPC .................... G06Q 50/22; G06Q 50/24; G06F 19/322–19/327; G16H 10/00; G16H 10/20; G16H 10/40; G16H 10/60; G16H 10/65; G16H 15/00; G16H 20/00; G16H 20/10; G16H 20/13; G16H 20/17; G16H 20/30; G16H 20/40; G16H 20/60; G16H 20/70; G16H 20/90; G16H 30/00
(Continued)

(56) References Cited

U.S. PATENT DOCUMENTS 3,989,034 A    11/1976 Hojaiban
5,042,503 A    8/1991 Torok et al.
(Continued)

FOREIGN PATENT DOCUMENTS

CA    2640855    6/2009
CA    2545339    7/2014
(Continued)

OTHER PUBLICATIONS

Hamilton, E. Et al. "A Comprehensive Labour Surveillance System," *J. of Perinatal Medicine*, vol. 15, Supplemental 1, (1987), pp. 144.
(Continued)

*Primary Examiner* — Christopher L Gilligan

(57) ABSTRACT

A graphical user interface is provided displaying a first viewing window selected from a set of possible viewing windows conveying respective feature measurements related to labor progression. At least one viewing window in the set of possible viewing windows conveys a given feature measurement and a safety limit associated to the given feature measurement. The graphical user interface also displays at least one control allowing a user to select a subset of viewing windows from the set of possible viewing windows, the subset of viewing windows including at least one viewing window other than the first viewing window. The selected subset of viewing windows is displayed simultaneously with the first viewing window. In response to the given feature measurement exceeding the associated safety limit, information is displayed to attract the attention of the user to the viewing window conveying the given feature measurement.

30 Claims, 9 Drawing Sheets

(51) Int. Cl.
    G16H 20/00      (2018.01)
    G16H 40/63      (2018.01)
    A61B 5/024      (2006.01)
    A61B 5/00       (2006.01)
    G06F 19/00      (2018.01)
    G06Q 50/22      (2018.01)
    A61B 5/0444     (2006.01)
    A61B 8/02       (2006.01)
    A61B 8/08       (2006.01)
    A61B 5/03       (2006.01)

(52) U.S. Cl.
    CPC .......... *A61B 5/0444* (2013.01); *A61B 5/4356* (2013.01); *A61B 5/4362* (2013.01); *A61B 5/742* (2013.01); *A61B 5/7445* (2013.01); *A61B 8/02* (2013.01); *A61B 8/0866* (2013.01); *G06F 19/00* (2013.01); *G06F 19/3418* (2013.01); *G06Q 50/22* (2013.01); *A61B 5/033* (2013.01); *A61B 5/7435* (2013.01)

(58) Field of Classification Search
    USPC .................................................. 705/2, 3, 4
    See application file for complete search history.

(56)            References Cited

U.S. PATENT DOCUMENTS

| | | | |
|---|---|---|---|
| 5,069,218 A | 12/1991 | Ikeda | |
| 5,088,497 A | 2/1992 | Ikeda | |
| 5,483,970 A | 1/1996 | Rosenberg | |
| 6,254,537 B1* | 7/2001 | Nguyen | 600/300 |
| 6,423,016 B1 | 7/2002 | Hamilton et al. | |
| 6,907,284 B2 | 6/2005 | Hamilton et al. | |
| 7,113,819 B2 | 9/2006 | Hamilton et al. | |
| 8,870,793 B2 | 10/2014 | Hamilton | |
| 2002/0083075 A1* | 6/2002 | Brummel et al. | 707/102 |
| 2002/0193670 A1* | 12/2002 | Garfield et al. | 600/304 |
| 2003/0187364 A1 | 10/2003 | Hamilton et al. | |
| 2003/0208128 A1 | 11/2003 | Hamilton et al. | |
| 2004/0133115 A1 | 7/2004 | Hamilton et al. | |
| 2004/0254430 A1* | 12/2004 | Hamilton | 600/300 |
| 2005/0049509 A1 | 3/2005 | Mansour et al. | |
| 2005/0267376 A1* | 12/2005 | Marossero et al. | 600/511 |
| 2007/0255588 A1 | 11/2007 | Hamilton | |
| 2008/0039744 A1 | 2/2008 | Hamilton | |
| 2009/0240158 A1 | 9/2009 | Hamilton et al. | |
| 2009/0259133 A1 | 10/2009 | Wolfberg et al. | |

FOREIGN PATENT DOCUMENTS

| | | |
|---|---|---|
| DE | 27 41 344 | 3/1979 |
| DE | 37 29 760 | 3/1989 |
| DE | 198 22 250 | 11/1999 |
| EP | 0 286 731 A1 | 10/1988 |
| EP | 0 306 915 | 3/1989 |
| EP | 0 808 603 | 11/1997 |
| EP | 0 286 731 A1 | 10/1998 |
| EP | 1 161 921 | 12/2001 |
| EP | 1 852 065 A1 | 11/2007 |
| EP | 1 852 065 B1 | 9/2011 |
| EP | 1 852 060 B1 | 12/2013 |
| WO | 01/93752 | 12/2001 |
| WO | 2004/041059 | 5/2004 |
| WO | WO 2005/015451 A1 | 2/2005 |

OTHER PUBLICATIONS

World Health Organization Partograph in Management Labour, *The Lancet*, vol. 343, (1994) pp. 1399-1404.
World Health Organization, Division of Family Health, geneva, Maternal Health and Safe Motherhood Programme, "The Partograph: The Application of the WHO Partograph in the Management of Labour," Copyright World Health Organization, Geneva, Switzerland (1994), pp. i-xviii and pp. 1-7.
Hamilton, Emily, et al., "Labor Pains, Unraveling the Complexity of OB Decision Making", *Crit Care Nurs Q*, vol. 29, No. 4, pp. 342-353, 2006.
A Written Opinion of the International Searching Authority mailed in connection with International Appln. No. PCT/CA2006/000417 dated Jul. 5, 2006 (7 pages).
A Declaration of Non-Establishment of International Search Report mailed in connection with International Appln. No. PCT/CA2006/000417 dated Jul. 5, 2006 (2 pages).
A Communication Pursuant to Article 94(3) EPC mailed in connection with European Patent Appln. No. 07290544.1-2305 dated Jun. 2, 2008 (2 pages).
A Communication Pursuant to Article 94(3) EPC mailed in connection with European Patent Appln. No. 07290533.4-2305 dated Jun. 3, 2008 (2 pages).
Espacenet English abstract of EP 0 286 731 A1.
International Preliminary Report on Patentability dated Jun. 24, 2010 in connection with International Patent Application No. PCT/CA2008/002134.
Office Action dated Apr. 14, 2010 in connection with U.S. Appl. No. 11/716,496.
Office Action dated May 17, 2010 in connection with U.S. Appl. No. 11/330,942.
Office Action dated Jul. 26, 2010 in connection with U.S. Appl. No. 11/330,942.
Notice of Allowance dated Mar. 24, 2011 in connection with European Patent Application No. EP 07 290 533.4 (5 pages).
Office Action dated Mar. 1, 2011 in connection with U.S. Appl. No. 12/285,617 (7 pages).
Non-Final Office Action dated Feb. 23, 2011 in connection with European Patent Application No. 07 290 544.1 (4 pages).
Final Office Action dated Feb. 7, 2011 in connection with U.S. Appl. No. 11/330,942 (11 pages).
Final Office Action dated Dec. 21, 2010 in connection with U.S. Appl. No. 11/716,496 (36 pages).
Final Office Action dated Oct. 3, 2011 in connection with U.S. Appl. No. 12/285,617.
Non-final Office Action dated Mar. 18, 2013 in connection with U.S. Appl. No. 12/747,022 (14 pages).
Examiner's Report (i.e., Office Action) issued by the Canadian Intellectual Property Office dated May 3, 2013 in connection with Canadian Patent Application No. 2,610,393 (6 pages).
Sallam, H.N., et al., "Mathematical relationships between uterine contractions, cervical dilation, descent and rotation in spontaneous vertex deliveries", International Journal of Gynecology & Obstetrics, vol. 64, Issue 2, Feb. 1, 1999, pp. 135-139.
Friedman, E.A., "Graphic Analysis of Labor", American Journal of Obstetrics & Gynecology, vol. 68, 1954, pp. 1568-1575.
Notice of Allowance issued by the European Patent Office dated Jul. 11, 2013 in connection with European Patent Application Serial No. 07290544.1, 5 pages.
Notice of Allowance issued by the United States Patent and Trademark Office dated Sep. 17, 2013 in connection with U.S. Appl. No. 11/330,942, 6 pages.
Non-Final Office Action issued by the United States Patent and Trademark Office dated Jun. 19, 2013 in connection with U.S. Appl. No. 11/716,496, 37 pages.
Final Office Action issued by the United States Patent and Trademark Office dated Jun. 20, 2013 in connection with U.S. Appl. No. 12/747,022, 16 pages.
Examiner's Report dated Dec. 18, 2013 in connection with Canadian Patent Application No. 2,610,393—8 pages.
Examiner's Report dated Dec. 20, 2013 in connection with Canadian Patent Application No. 2,581,910—8 pages.
Non-Final Office Action dated Apr. 2, 2014 in connection with U.S. Appl. No. 12/747,022—15 pages.
Notice of Allowance dated Jul. 3, 2014 in connection with U.S. Appl. No. 14/036,188—7 pages.
Examiner's Report dated Feb. 27, 2015 in connection with Canadian Patent Application No. 2,640,855—3 pages.

(56) References Cited

OTHER PUBLICATIONS

Notice of Allowance dated Sep. 30, 2015 in connection with Canadian Patent Application No. 2,581,910—1 page.
Examiner's Answer to Appeal Brief dated Nov. 19, 2015 in connection with U.S. Appl. No. 12/747,022—17 pages.
Examiner's Report dated Feb. 9, 2016 in connections with Canadian Patent Application No. 2,640,855—3 pages.
Notice of Allowance dated Feb. 8, 2016 in connection with Canadian Patent Application No. 2,707,312—1 page.
Board Decision dated Dec. 29, 2016 in connection with U.S. Appl. No. 11/716,496—8 pages.
Examiner's Report (Final Action) dated Dec. 19, 2016 in connection with Canadian Patent Application No. 2,610,393—5 pages.
Non-Final Office Action dated Dec. 8, 2014 in connection with U.S. Appl. No. 12/747,022—14 pages.
Examiner's Report dated Dec. 18, 2014 in connection with Canadian Patent Application No. 2,581,910—3 pages.
Examiner's Report dated Jan. 26, 2015 in connection with Canadian Patent Application No. 2,707,312—4 pages.
Patent and Trial Appeal Board (PTAB) decision issued on Sep. 1, 2017 in connection with U.S. Appl. No. 12/747,022.
Office Action issued by the Canadian Intellectual Property Office dated Jun. 8, 2012 in connection with Canadian Patent Application No. 2,610,393.
Office Action issued by the Canadian Intellectual Property Office dated Jul. 24, 2012 in connection with Canadian Patent Application No. 2,545,339.
Henriksen K., Battles JB, Marks ET, et al.,"Diagnosing Diagnosis Errors: Lessons from a Multi-institutional Collaborative Project", Advances in Patient Safety: From Research to Implementation, vol. 2: Concepts and Methodology, Feb. 2005, 21 pages.
Nunes .I, Ayres-de-Campos D., "Computer analysis of foetal monitoring signals", Best Practice and Research Clinical Obstetrics and Gynaecology (2015), http://dx.doi.org/10.1016/j.bpobgyn.2015.02.009, pp. 1 to 11.
Simpson et al., "Patient Safety Implications of Electronic Alerts and Alarms of Maternal-Fetal Status During Labor", Nursing for Women's Health (2016), vol. 20, Issue 4, pp. 358 to 366.
Non-Final Office Action dated May 1, 2017 in connection with U.S. Appl. No. 11/716,496.
Notice of Allowance dated Jun. 19, 2017 in connection with U.S. Appl. No. 11/716,496.
Examiner's Report issued by the Canadian Intellectual Property Office in connection with Canadian patent application No. 2,970,898 dated Jun. 6, 2018—6 pages.

* cited by examiner

METHOD AND SYSTEM FOR MONITORING LABOUR PROGRESSION FOR AN OBSTETRICS PATIENT

FIELD OF THE INVENTION

The present invention relates generally to the field of obstetrics, and more specifically to a method and apparatus for monitoring labor progression and for providing a user interface to display data conveying maternal and fetal information during labor.

BACKGROUND

Birth related injuries are rare but devastating events because the consequences can lead to lifelong impairment for the baby, family and society in general. During labor, clinical staff monitors various health characteristics of the obstetrics patients in order to obtain a qualitative assessment of the mother's and the fetus's well-being. The clinical staff uses visual methods to study the heart rate tracings of the fetus and mother and the measurements and relies on their experience to deduce the degree of maternal and fetal well being and to assess whether labour is progressing normally. Low incidence-high consequence injuries are particularly challenging to prevent. Because of their rarity, it is difficult for clinicians to remain vigilant, to develop substantial experience with them and to maintain the appropriate skills. Over-caution can result in a high rate of unnecessary interventions in the majority of patients who are not at risk for the rare adverse event.

In addition, several working conditions known to promote error in judgement are prevalent in obstetrics. Fatigue, a well-known error producing condition, is common. Frequent false alarms, because the warning signs are numerous and nonspecific, lead to complacency and missed recognition of a true problem. Workload is unpredictable and heavy demands may divert the teams focus from a developing problem. The required assessments are numerous and complex. Clinicians must integrate many pieces of information pertaining to both the mother and the baby's conditions, over prolonged periods of time, communicate their assessments clearly among team members and implement corrective measures before it is too late. Moreover, the conditions present in one birth may be quite different from another such that a particular observation may be normal under one set of circumstances and abnormal for another.

Although many metrics have been developed, a deficiency associated with existing approaches to labour monitoring is that they do not provide suitable functionality for allowing the clinical staff to effectively manage and make use of the large amount of information gathered during labour progression. As such, the clinical staff is frequently overloaded with information. This overload of information often obscures the more crucial facts and makes critical information difficult to discern. To date, there exists no suitable tool or system for allowing the clinical staff to view a concise representation of labour progression for an obstetrics patient.

In the context of the above, there is a need in the industry to provide a method and device for displaying data conveying labor related information for an obstetrics patient that alleviates at least in part problems associated with the existing methods and devices.

SUMMARY

In accordance with a broad aspect, the invention provides a computer readable storage medium storing a program element suitable for execution by a CPU where the program element implements a graphical user interface module for displaying labour related information. The graphical user interface module is adapted for displaying a first viewing window selected from a set of possible viewing windows, each viewing window in the set of possible viewing windows conveying a feature measurement related to labour progression. At least one viewing window in the set of possible viewing windows conveys a given feature measurement and a safety limit associated to the given feature measurement. The graphical user interface module is adapted for displaying at least one control allowing a user to select a subset of viewing windows from the set of possible viewing windows, the subset of viewing windows including at least one viewing window other than the first viewing window. The graphical user interface module is adapted for displaying the selected subset of viewing windows simultaneously with the first viewing window. In response to the given feature measurement exceeding the safety limit associated to the given feature measurement, the graphical user interface module is adapted for displaying information to attract the attention of the user to the viewing window conveying the given feature measurement.

An advantage of the present invention is that it allows a user to view simultaneously multiple information elements related to labor progression thereby increasing the clinical staff's situational awareness by allowing the clinical staff to assess more consistently how labour is progressing by taking into account multiple information elements. In addition, but providing a safety limit for a feature measurement, the user can readily observe whether the feature is within or exceed the safety limit.

Another advantage of the present invention allows a user to select which information elements to view for a given obstetrics patient. This provides the user with flexibility regarding what is being observed such that information elements considered to be more important by the user may be displayed and those considered of lesser importance may be concealed. As such, the clinical staff can view a concise representation of labor related information for an obstetrics patient.

In accordance with a specific implementation, the safety limit associated to the given feature measurement includes at least one threshold value.

In a first specific implementation, the graphical user interface module displays a visual indicator in association with the viewing window conveying the given feature measurement when the given feature measurement exceeds the at least one threshold value. The visual indicator may be represented in any suitable manner. In a specific implementation, the threshold value corresponds to a boundary value set by best practices or by a healthcare establishment (eg. hospital) policy.

In a second specific implementation the graphical user interface module is adapted to display the viewing window conveying the given feature measurement when the given feature measurement exceeds the at least one threshold value. The at least one threshold value may be conveyed in textual or graphical form in the associated viewing window.

In accordance with a specific implementation, the control allows the user to select the subset of the set of windows by using an input device selected from the set consisting of a mouse, keyboard, pointing device, speech recognition unit and touch sensitive screen. In a specific implementation the control includes a selection box. In an alternative implementation, the graphical user interface module is adapted for displaying a set of controls, each control in said set of controls being associated to a respective viewing window in the set of possible viewing windows, each control allowing a user to select an associated viewing window.

In accordance with another broad aspect, the invention provides an apparatus for implementing a user interface for displaying labour related information. The apparatus comprises an input for receiving signals conveying labour information and a processing unit in communication with the input. The processing unit is operative for implementing a graphical user interface module for displaying labour related information. The graphical user interface module is adapted for displaying a first viewing window selected from a set of possible viewing windows. Each viewing window in the set of possible viewing windows conveys a feature measurement related to labour progression derived at least in part from the signals received at the input. At least one viewing window in the set of possible viewing windows conveys a given feature measurement and a safety limit associated to the given feature measurement. The graphical user interface module is also adapted for displaying at least one control allowing a user to select a subset of viewing windows from the set of possible viewing windows, the subset of viewing windows including at least one viewing window other than the first viewing window. The graphical user interface module is also adapted for displaying the selected subset of additional viewing windows simultaneously with the first viewing window. In response to the given feature measurement exceeding the safety limit associated to the given feature measurement, the graphical user interface module is also adapted for displaying information to attract the attention of the user to the viewing window conveying the given feature measurement. The apparatus also includes an output in communication with the processing unit suitable for releasing a signal for causing a display unit to display the graphical user interface module.

In accordance with another broad aspect, the invention provides a method for displaying labour related information. The method comprises receiving signals conveying labour information. The method also comprises displaying a first viewing window selected from a set of possible viewing windows, each viewing window in the set of possible viewing windows conveying a feature measurement related to labour progression derived at least in part from the signals received. At least one viewing window in the set of possible viewing windows conveys a given feature measurement and a safety limit associated to the given feature measurement. The method also comprises displaying at least one control allowing a user to select a subset of viewing windows from the set of possible viewing windows, the subset of viewing windows including at least one viewing window other than the first viewing window. The method also comprises displaying the selected subset of viewing windows simultaneously with the first viewing window. The method also comprises displaying information to attract the attention of the user to the viewing window conveying the given feature measurement in response to the given feature measurement exceeding the safety limit associated to the given feature measurement.

In accordance with another broad aspect, the invention provides a labour monitoring system comprising a first sensor for receiving a signal indicative of a fetal heart rate, a second sensor for receiving a uterine contraction signal associated with an obstetrics patient, an apparatus for implementing a user interface for displaying labour related information and a display unit. The apparatus includes a first input in communication with the first sensor for receiving the fetal heart rate signal. The apparatus also includes a second input in communication with the second sensor for receiving the uterine contraction signal. The apparatus also includes a processing unit in communication with the first input and the second input and operative for implementing a graphical user interface module for displaying labour related information. The graphical user interface module is adapted for displaying a first viewing window selected from a set of possible viewing windows. Each viewing window in the set of possible viewing windows conveys a feature measurement related to labour progression derived at least in part from the signals received at the first input and the second input. At least one viewing window in the set of possible viewing windows conveys a given feature measurement and a safety limit associated to the given feature measurement. The graphical user interface module is also adapted for displaying at least one control allowing a user to select a subset of viewing windows from the set of possible viewing windows, the subset of viewing windows including at least one viewing window other than the first viewing window. The graphical user interface module is also adapted for displaying the selected subset of additional viewing windows simultaneously with the first viewing window. In response to the given feature measurement exceeding the safety limit associated to the given feature measurement, the graphical user interface module is adapted for displaying information to attract the attention of the user to the viewing window conveying the given feature measurement. The apparatus also includes an output in communication with the processing unit, wherein the output is suitable for releasing an output signal for causing a display unit to display the graphical user interface module. The display unit of the labour monitoring system is in communication with the output of the apparatus and is responsive to the output signal to display the graphical user interface module.

In accordance with another broad aspect, the invention provides a client system adapted for communication with a server system for implementing a graphical user interface module for displaying labour related information for an obstetrics patient. The client system and the server system are operative to exchange messages over a data network. The client system is adapted for receiving from the server system a program element for causing a graphical user interface module to be displayed at the client system. The graphical user interface module is adapted for displaying a first viewing window selected from a set of possible viewing windows, each viewing window in the set of possible viewing windows conveying a feature measurement related to labour progression. At least one viewing window in the set of possible viewing windows conveys a given feature measurement and a safety limit associated to the given feature measurement. The graphical user interface module is also adapted for displaying at least one control allowing a user to select a subset of viewing windows from the set of possible viewing windows, the subset of viewing windows including at least one viewing window other than the first viewing window. The client system is adapted for transmitting data indicative of the selected subset of the set of possible viewing windows to the server system. The client system is also adapted for receiving from the server system instructions for causing the selected subset of viewing windows to be displayed simultaneously with the first viewing window. The client system is also adapted for receiving from the server system instructions for causing information to be displayed to attract the attention of the user to the viewing window conveying the given feature measurement in response to the given feature measurement exceeding the safety limit associated to the given feature measurement.

In accordance with specific implementations the data network may be of any suitable network configuration including Intranets and the Internet.

In accordance with another broad aspect, the invention provides an apparatus for implementing a user interface for displaying labour related information. The apparatus comprises means for receiving signals conveying labour information. The apparatus also comprises means for implementing a graphical user interface module for displaying labour related information. The graphical user interface module is adapted for displaying a first viewing window selected from a set of possible viewing windows. Each viewing window in the set of possible viewing windows conveys a feature measurement related to labour progression derived at least in part from the signals received. At least one viewing window in the set of possible viewing windows conveys a given feature measurement and a safety limit associated to the given feature measurement. The graphical user interface module is also adapted for displaying at least one control allowing a user to select a subset of viewing windows from the set of possible viewing windows, the subset of viewing windows including at least one viewing window other than the first viewing window. The graphical user interface module is also adapted for displaying the selected subset of additional viewing windows simultaneously with the first viewing window. In response to the given feature measurement exceeding the safety limit associated to the given feature measurement, the graphical user interface module displays information to attract the attention of the user to the viewing window conveying the given feature measurement. The apparatus also comprises means for releasing a signal for causing a display unit to display the graphical user interface module.

In accordance with yet another broad aspect, the invention provides a computer readable storage medium storing a program element suitable for execution by a CPU, the program element implementing a graphical user interface module for displaying labour related information. The graphical user interface module is adapted for displaying a first viewing window selected from a set of possible viewing windows, each viewing window in the set of possible viewing windows conveying a feature measurement related to labour progression. The set of possible viewing windows includes at least one grouping having at least two viewing windows. The graphical user interface module is also adapted for displaying at least one control allowing a user to select a subset of viewing windows from the set of possible viewing windows and for displaying the selected subset of viewing windows simultaneously with the first viewing windows.

In accordance with yet another broad aspect, the invention provides a computer readable storage medium storing a program element suitable for execution by a CPU, the program element implementing a graphical user interface module for displaying labour related information. The graphical user interface module is adapted for receiving a signal conveying a user identifier associated to a user of the system. The graphical user interface module is also adapted for displaying a first viewing window selected from a set of possible viewing windows, each viewing window in the set of possible viewing windows conveying a feature measurement related to labour progression. The graphical user interface module is also adapted for displaying at least one additional viewing window other than the first viewing window. The additional viewing window is selected from the set of possible viewing windows at least in part on the basis of the signal conveying the user identifier. The graphical user interface module is also adapted for displaying at least one control allowing a user to select a subset of viewing windows from the set of possible viewing windows and for displaying the selected subset of viewing windows simultaneously with the first viewing window and with the at least one additional viewing window.

These and other aspects and features of the present invention will now become apparent to those of ordinary skill in the art upon review of the following description of specific embodiments of the invention in conjunction with the accompanying drawings.

Other aspects and features of the present invention will become apparent to those ordinarily skilled in the art upon review of the following description of specific embodiments of the invention in conjunction with the accompanying figures.

DETAILED DESCRIPTION

Figure 1:
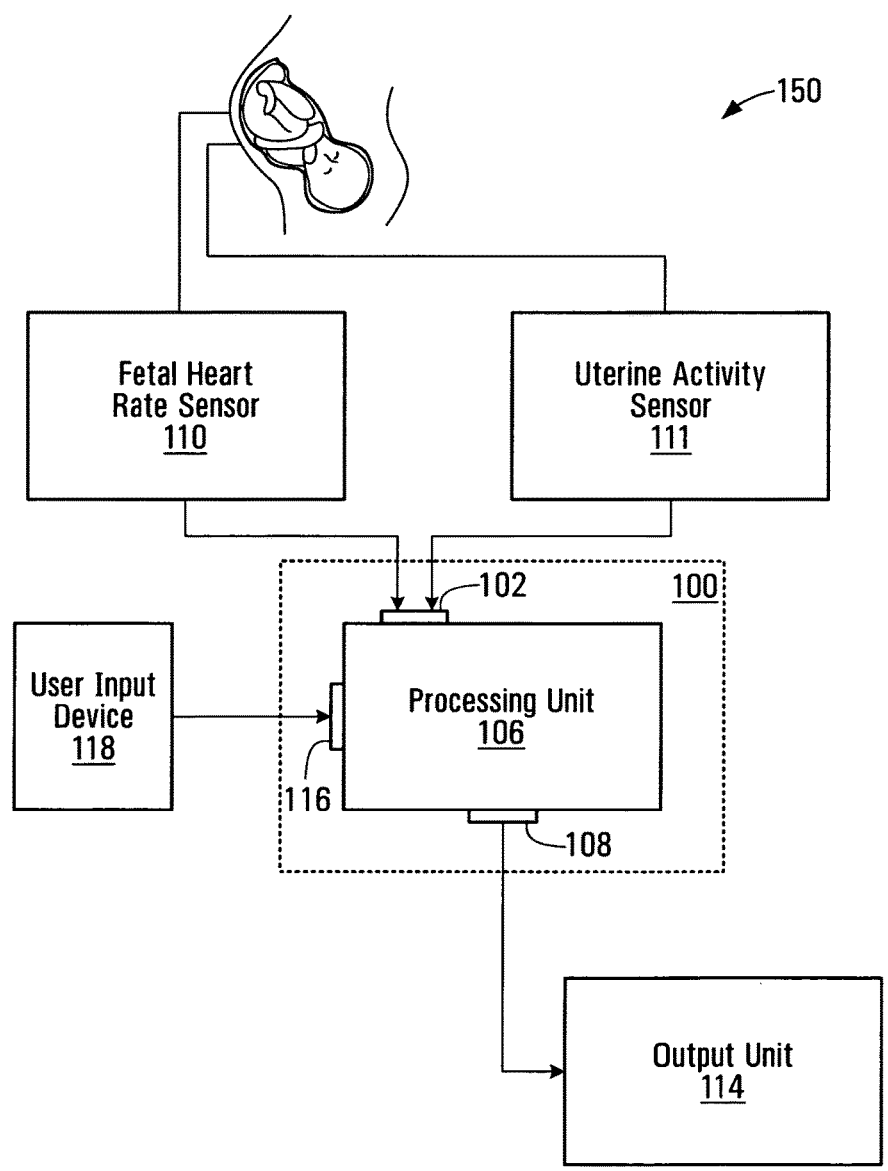
FIG. 1 shows a high-level functional block diagram of a system including a processing unit for monitoring labour for an obstetrics patient in accordance with a specific example of implementation of the present invention.

With reference to FIG. 1, there is shown a configuration of a system 150 for monitoring labor progress for an obstetrics patient comprising a fetal heart rate sensor 110, a uterine activity sensor 111, a user input device 118, an apparatus 100 implementing a user interface for displaying labour related information and an output unit 114.

The user input device 118 is for receiving data from a user of the system. The data may convey commands directed to controlling various features of the user interface implemented by apparatus 100 and, optionally, may also convey various measurements associated with the obstetrics patients taken during labour. The type of data received through input device 118 may vary depending on the type of information that the apparatus 100 is adapted to process and interpret. In a specific example of implementation, input device 118 allows a user to enter a selection regarding additional viewing windows to be displayed on the graphical user interface implemented by apparatus 100. Optionally, input device 118 allows a user to a user identifier associated to the user. Other specific examples of the type of information that may be provided through input device 118 will be described later on in the specification. The user input device 118 includes any one or a combination of the following: keyboard, pointing device, touch sensitive surface, actuator/selection switches or speech recognition unit.

The fetal heart rate sensor 110 is for detecting a fetal heart rate of a fetus in-utero, also referred to as a fetus in the womb. The fetal heart rate sensor 110 samples the fetal heart rate at a certain pre-determined frequency to generate the signal indicative of the fetal heart rate. Fetal heart rate sensors are well known in the art to which this invention pertains and any suitable sensor for detecting a fetal heart rate may be used without detracting from the spirit of the invention and as such will not be described further here.

The uterine activity sensor 111 is for monitoring uterine activity (TOCO). The sensor samples the contraction pattern at a certain pre-determined frequency to generate the signal indicative of uterine activity. Sensors for monitoring uterine activity are well known in the art to which this invention pertains and any suitable sensor may be used without detracting from the spirit of the invention and as such will not be described further here.

Optionally, the fetal monitoring system 150 may include other sensors (not shown) for measuring labour progress and the fetus' tolerance to labour. Such sensors may include for example:
- a sensor for measuring the maternal oxygen saturation
- a sensor for measuring the foetal oxygen saturation
- a sensor for measuring maternal blood pressure Suitable sensors other than the ones described above may be used without detracting from the spirit of the invention.

The output unit 114 is coupled to the apparatus 100 and receives a signal causing the output unit 114 to display a graphical user interface module implemented by apparatus 100. The output unit 114 may be in the form of a display screen, a printer or any other suitable device for conveying to the physician or other health care professional the progression of labour related information. In a non-limiting implementation, the output unit 114 includes one or more display monitors to display the graphical user interface. The output unit 114 may also include a printer device for providing a paper print out of the graphical user interface implemented by apparatus 100.

The apparatus 100 includes a first input 102, a second input 116, a processing unit 106 and an output 108. The first input 102 is for receiving signals conveying labour information. In the example depicted the first input is for receiving a fetal heart rate signal from the fetal heart rate sensor 110 and the uterine activity signal from the uterine activity sensor 111. It will be readily appreciated that, although the fetal heart rate signal and the uterine activity signal are received at a same input 102 in the embodiment illustrated in the figures, the signals may be provided to processing unit 106 through separate inputs without detracting from the spirit of the invention. The second input 116 is for receiving data from a user through input device 118. The processing unit 106 processes the signals received at input 102 as well as the user data received at input 116 and to derive various information elements related to labour progression. The processing unit 106 also implements a graphical user interface module for displaying labour related information associated to the obstetrics patient. The output 108 is for releasing a signal for causing output unit 114 to display the graphical user interface module implemented by processing unit 106.

Processing Unit 106

Figure 2:
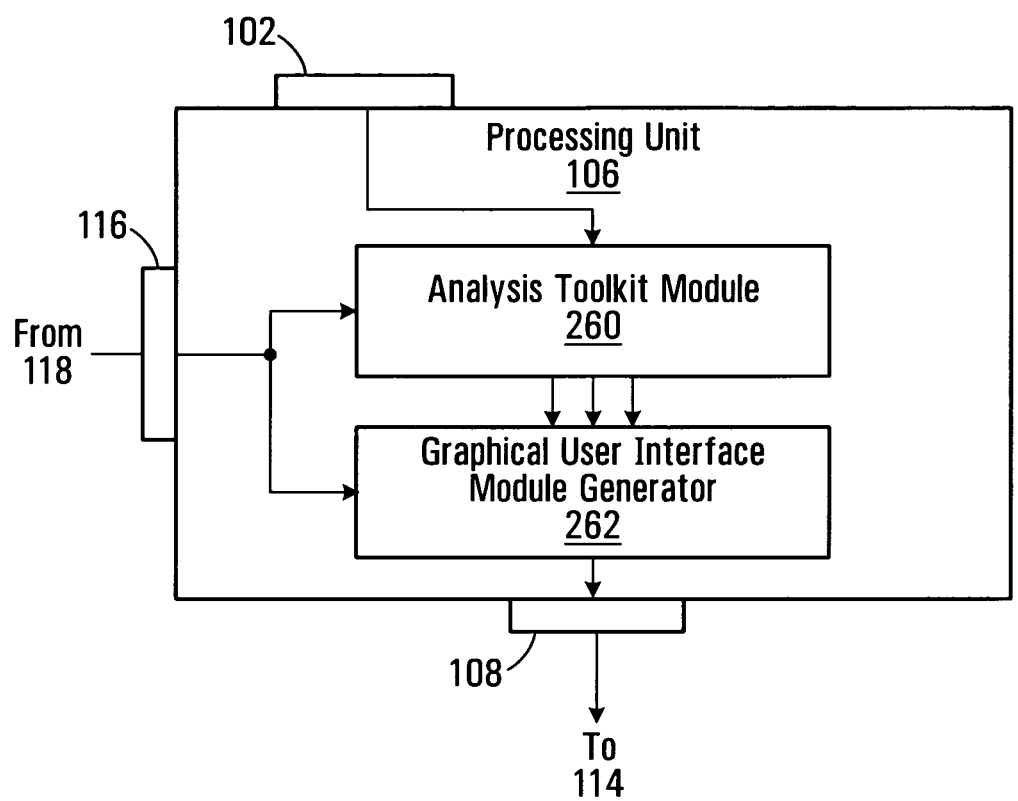
FIG. 2 shows a block diagram of the processing unit depicted in FIG. 1 in accordance with a specific example of implementation of the present invention.

A specific example of implementation of the processing unit 106 of apparatus 100 is depicted in greater detail in FIG. 2 of the drawings. As shown, the processing unit 106 includes two sub-components namely an analysis toolkit module 260 and a graphical user interface module generator 262.

The analysis toolkit module 260 includes a set of processing entities adapted for receiving data from the fetal heart rate sensor 110, the uterine activity sensor 111 and the input device 118 and processing that data to derive therefrom various information elements related to labour progression.

In a non-limiting implementation, the analysis toolkit module 260 may be viewed as a grouping of analysis tools, each tool being operative for deriving one or more information elements related to labour progression. Examples of the types of tools that may be part of the analysis toolkit module 260 are described below. In addition, certain embodiments of the invention may be configured such that the analysis toolkit module 260 is adapted to be augmented with additional tools. Such a modular configuration is particularly advantageous as it allows the new tools to be added as new developments arise. Such a modular configuration is also advantageous as it allows the end user to customise the system 150 (FIG. 1) so that it includes the desired tools and conveys the desired information.

In a specific example of implementation, the analysis toolkit module 260 includes a tool for deriving over time levels of risk associated with the labour progression. Any suitable tool for deriving a level of risk may be used. In a very specific example, the level of risk associated with labour progression is derived on the basis of method described in U.S. patent application Ser. No. 10/113,788 filed on Apr. 1, 2002 and presently pending and assigned to LMS Medical Systems Ltd. The content of the above noted document is incorporated herein by reference. In this document a method for monitoring the condition of a fetus to assess a degree of risk of developing a permanent neurological condition is described. The degree of risk of developing a permanent neurological condition is expressed as a likelihood that the condition of the fetus belongs to a class in a group of classes, where each class in the group of classes is associated with a pre-defined fetal condition. Other methods for deriving a level of risk associated with labour progression may be used without detracting from the spirit of the invention. The tool for deriving levels of risk associated with the labour progression releases these information elements over time for transmission to the graphical user interface module generator 262.

In a specific example of implementation, the analysis toolkit module 260 includes a tool for deriving an expected cervical dilation over time. In a non-limiting example of implementation, the expected dilation of the cervix over time is derived on the basis of method described in U.S. Pat.

No. 6,423,016 issued Jul. 23, 2002 and presently assigned to LMS Medical Systems Ltd. The content of the above noted document is incorporated herein by reference. In this document, a method for tracking the labor progress of a patient during childbirth is described for deriving an expected cervical dilation on the basis of a group of clinical measurements associated to a patient. The group of clinical measurements includes data elements indicative of a measurement of a previous dilation of the cervix of the patient, a contraction count, a previous level of descent of the child, a previous effacement measurement of the cervix, an epidural status and a parity status. The actual observed cervical dilations were plotted over time on a graph against a range of expected cervical dilation derived on the basis of the mathematical model which allows the clinical staff to assess whether the cervix was dilating in accordance with an expected progression as described by the model. The group of clinical measurements described above may be provided through input device 118 shown in FIG. 1 of the drawings. Other methods for deriving an expected cervical dilation may be used without detracting from the spirit of the invention. The tool for deriving expected cervical dilations releases these information elements over time for transmission to the graphical user interface module generator 262.

In a specific example of implementation, the analysis toolkit module 260 includes a tool for deriving fetal heart rate feature measurements. Fetal heart rate feature measurements include, for example, mean baseline, mean baseline variability, decelerations and accelerations amongst others. Any suitable tool for deriving fetal heart rate feature measurements may be used. The tool for deriving fetal heart rate feature measurements releases these measurements over time for transmission to the graphical user interface module generator 262.

In a specific example of implementation, the analysis toolkit module 260 also includes a tool for deriving a running average of a uterine contraction count associated with the obstetrics patient. More specifically the tool processes the signal received from the uterine activity sensor 111 to compute the running average of a uterine contraction count. Any suitable method for the compute the running average may be used. The tool for deriving the running average of the uterine contraction count releases these measurements over time for transmission to the graphical user interface module generator 262. Optionally, this tool also releases a data element indicative of a threshold average uterine contraction count. The threshold average contraction count may be set in accordance best practices and/or in accordance with hospital/care-giver facility policy.

In a specific example of implementation, the analysis toolkit module 260 includes a tool for allowing a user to select a portion of the fetal heart rate signal for display in a zoomed in fashion. A non-limiting example of such a tool is described in U.S. Pat. No. 6,907,284, entitled "Method and Apparatus for Displaying a Heart Rate Signal", which issued Jun. 14, 2005 and is presently assigned to LMS Medical Systems Ltd. The content of the above noted document is incorporated herein by reference. The tool for allowing a user to select a portion of the fetal heart rate signal for display in a zoomed in fashion releases data over time for transmission to the graphical user interface module generator 262.

In a specific implementation, at least some of the tools are adapted for generating information element indicating a safety limit for the metrics being measured and/or observed. The safety limit marks a boundary between measurements/observations considered to be safe or "normal" and measurements/observations considered as being associated to riskier situations. It will be readily apparent that multiple safety limits may be used for marking boundaries between different levels of risk (eg. low, intermediate, high etc. . . . ). The number of safety limits for a given measurement will typically depend on the type of measurement being observed. The safety limit(s) may be set in accordance best practices and/or in accordance with hospital/care-giver facility policy. The manner in which the safety limits are selected and well as the number of safety limits is not critical to the invention and as such will not be described further here.

It will be readily apparent that additional tools may be included in, and certain tools omitted from, the analysis toolkit module 260 without detracting from the spirit of the invention.

The graphical user interface module generator 262 will now be described in greater detail herein below.

Graphical Interface Module Generator 262

The graphical user interface module generator 262 is in communication with the analysis toolkit module 260 and receives therefrom over time a plurality of information elements related to labour progression. The graphical user interface module 262 also receives data indicative of user selection(s). The data may be directly received through input 116 or may be relayed through the analysis toolkit module 260.

The graphical user interface module generator 262 processes the plurality of information elements related to labour progression and the data indicative of user selection(s) to generate a graphical user interface module.

More specifically, the graphical user interface module generator 262 is adapted to generate a signal for displaying a first viewing window selected from a set of possible viewing windows. Each viewing window in the set of possible viewing windows conveys a feature measurement related to labour progression. One or more of the viewing windows in the set of possible viewing windows convey a given feature measurement and an associated safety limit. The graphical user interface module generator 262 generates a signal for displaying one or more controls allowing a user to select a subset of viewing windows from the set of possible viewing windows, the subset of viewing windows including at least one viewing window other than the first viewing window. In addition, the graphical user interface module generator 262 processes the plurality of information elements related to labour progression and the data indicative of user selection(s) to generate a signal for displaying a set of additional viewing windows as part of the graphical user interface module simultaneously with the first viewing window. In a specific implementation each additional viewing window is adapted to display information conveying one or more information elements related to labour progression. In the additional viewing windows, when the information elements vary over time, such information elements are preferably conveyed as tracings over time. The specific appearance of the graphical user interface module may vary from one implementation to the other. For example, the positions and general layout of the various viewing windows may be different from one implementation to the other. Also, certain implementations may show various components of the user interface module on different display screens instead of a same display screen.

In a first embodiment, the graphical user interface module generator 262 generates a signal, in response to a given feature measurement exceeding its associated safety limit, for displaying information to attract the attention of the user to a viewing window in the set of possible viewing windows conveying the given feature measurement.

In a second embodiment, the set of possible viewing windows includes at least one grouping, the at least one grouping including at least two viewing windows for allowing the user to select two (2) or more viewing windows simultaneously.

In a third embodiment, the graphical user interface module generator 262 generates a signal for displaying at least one additional viewing window other than the first viewing window selected from the set of possible viewing windows at least in part on the basis a user identifier.

In a specific implementation, the graphical user interface module generator 262 may be viewed as a group of display modules, each display modules in the group being associated to a corresponding one of the analysis tools in the analysis toolkit module 260. Each display module is adapted to generate a respective graphical representation in the form of viewing window of the information generated by the respective analysis tools. The graphical user interface module generator 262 also includes a consolidation module in communication with the display modules in the group of display modules for generating the graphical user interface.

Below are described specific examples of implementation of the graphical user interface module. The person skilled in the art, in light of the present specification, will readily appreciate that many variants are possible without detracting from the spirit of the invention.

First Example

Figure 3A:
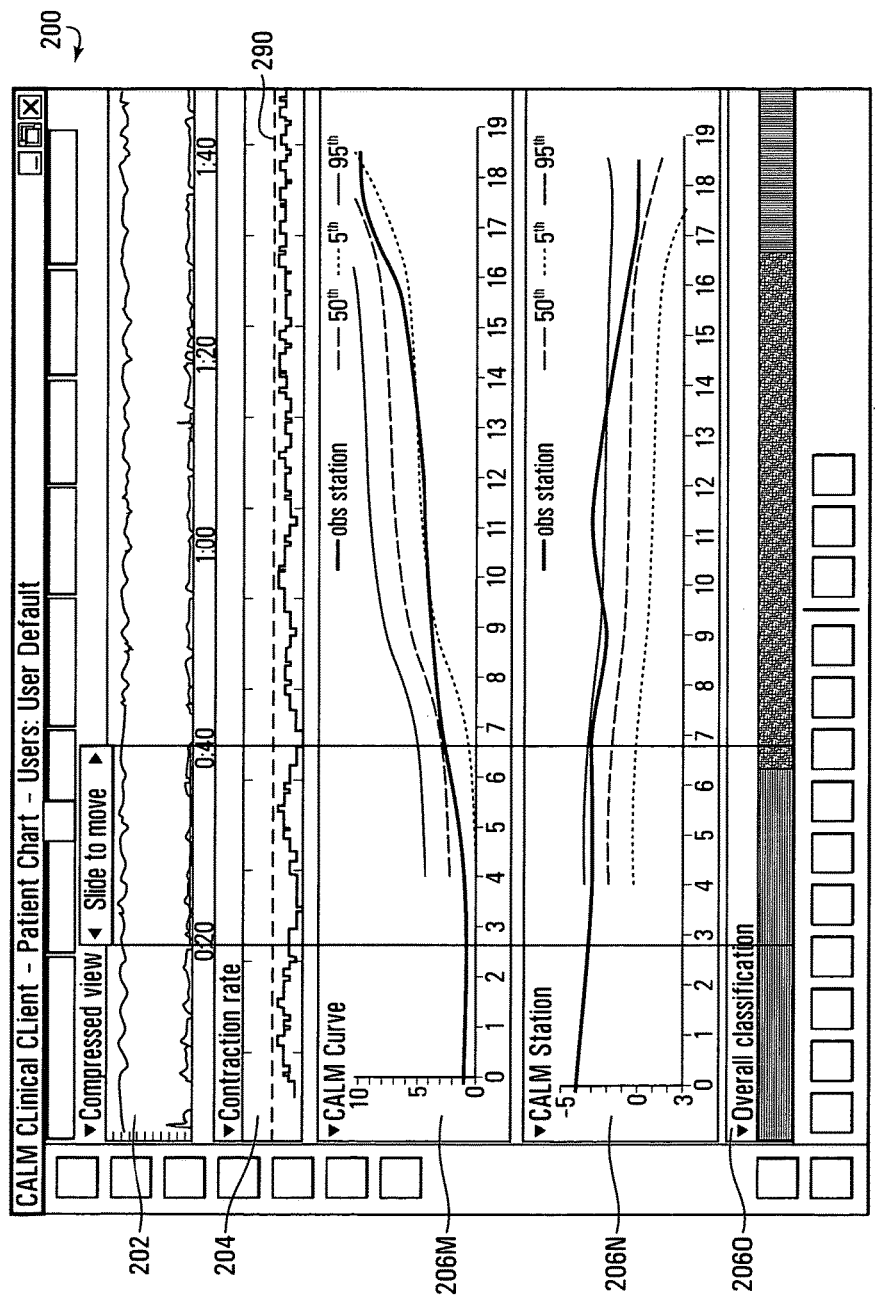
FIG. 3a shows a specific example of implementation of a graphical user interface implemented by the system shown in FIG. 1 for providing labour related information in accordance with a first non-limiting example of implementation of the invention.

With reference to FIG. 3a, a first specific example of a graphical user interface module 200 implemented by graphical user interface module generator 262 (shown in FIG. 2) is shown. The graphical user interface module 200 includes a first viewing window 202 and a second viewing window 204. In the first viewing window 202, a first tracing indicative of a fetal heart rate signal is displayed and in the second viewing window 204, a second tracing indicative of a uterine contraction pattern associated with the obstetrics patient is displayed. The graphical user interface module also includes a set of controls 206m-n-o for allowing a user to select for display additional viewing windows from a set of possible viewing windows. As described above, the additional viewing windows in the set of possible viewing windows are adapted for conveying various information elements related to the assessment of labour for the obstetrics patient. Such information elements were derived by the analysis toolkit module 260 (shown in FIG. 2). The graphical user interface module displays the selected subset of additional viewing windows simultaneously with the first viewing window 202 and, this example, second viewing window 204.

Advantageously, the above described graphical user interface allows a user to view simultaneously multiple information elements related to the labor progression. Another advantage of the present invention is that it allows a user to select which information elements to view for a given obstetrics patient. This provides the user with flexibility regarding what is being observed such that information elements considered to be more important by the user may be displayed and those considered of lesser importance may be fully or partially concealed on the display. This flexibility allows the clinical staff to assess more easily how labour is progressing by limiting the amount information that they are observing and need to process.

In the specific implementation depicted in FIG. 3a, the second tracing in the second viewing window 204 conveys a running average of a uterine contraction count associated with the obstetrics patient. The second viewing window 204 also includes information pertaining to a safety limit associated with the average of a uterine contraction count. The safety limit includes a threshold uterine contraction count illustrated a third tracing 290. In the example depicted, the threshold value is depicted by a dotted line positioned along a certain contraction count. The threshold value 290 marks a boundary between uterine contraction counts considered to be normal and contraction count considered as being associated to riskier situations. Optionally, the graphical user interface module is adapted for displaying a visual indicator in association with the second viewing window 204 when the running average of the uterine contraction count associated with the obstetrics patient exceeds the threshold uterine contraction count 290. Any suitable type of visual indicator may be used to draw attention to the additional viewing window 204. Examples of visual indicators that may be used include, without being limited to:

Variations in color. For example, a color scheme may be established whereby certain colors are associated with varying levels of risk. Portions of the window may turn a certain color associated with a high level of risk when the fetal heart rate feature measurement exceeds an associated threshold value. A non-limiting example of a color scheme is green=normal; yellow: intermediate risk level; red: high level of risk however any suitable color scheme may be used;

Variation in display intensity of the viewing window. For example, flashing or blinking of the viewing window may be used as a visual indicator to draw attention;

Variation in the size of the size or position of the viewing window. For example, the appearance of the viewing window may be made to appear more prominently on the user interface or at a location that is more likely to draw the attention of the clinical staff;

Causing the viewing window to be displayed or expanded. For example, in the case where the viewing window is not displayed on the user interface or is in collapsed form, automatically causing the viewing window to be displayed or expanded;

Displaying a message prompting/alerting the clinical staff to observe what is going on in the additional viewing window 204.

Although the above described example of visual indicators have been described in the context of drawing attention to the additional viewing window 204, similar types of visual indicators may be used for drawing attention other viewing windows in a set of addition viewing windows. In an alternative embodiment, an audio signal, alone or in combination with the visual indicator, may be used to draw attention to an additional viewing window displaying a feature that has exceeded its associated safety limit.

In the example depicted in FIG. 3a, the graphical user interface module is depicted as including a set of controls 206m-o each of which, when actuated, displays or conceals an associated additional viewing window. Each control 206m-o is associated to respective feature measurements related to labour progression. In the example shown, the additional viewing windows associated to controls 206m, 206n, 206o are displayed simultaneously with the first viewing window 202 and second viewing window 204. In a specific example of implementation, whether the additional viewing windows associated to controls 206m, 206n, 206o convey information related to labor progression over time, the viewing windows are time aligned such as to allows the user to view the various information over the same time period.

In the example depicted in FIG. 3a, an additional viewing window is displayed conveying information related to the expected dilation of the cervix over time. This additional viewing window is associated with control 206m. More specifically, the additional viewing window displays over time the expected dilation of the cervix. This information is derived by the corresponding tool in the analysis toolkit module 260.

Although the controls 206m-o depicted in FIG. 3a are shown in association with a set of additional viewing windows that can be displayed or concealed, it will be appreciated that the control may be of any suitable form for allowing the user to select a subset of a set of additional viewing windows. For example, the control may be comprised of text boxes, drop down menus, handles, images (eg. icons) or any other suitable means on the user interface. The user may provide his selection through the user input device 118 which may be any one or a combination of the following: keyboard, pointing device, touch sensitive surface or speech recognition unit.

Specific examples of the type of controls that may be used in practical implementations will now be described with reference to FIGS. 4a and 4b.

Figure 4A:
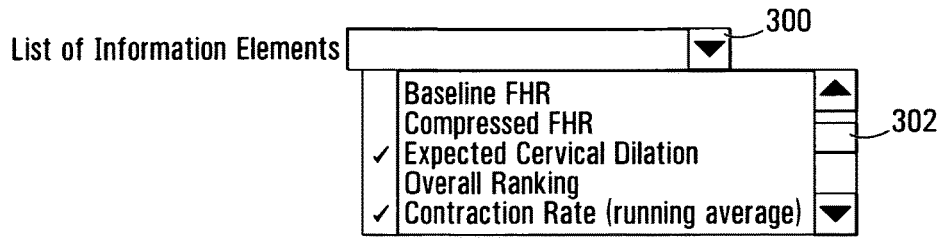
FIGS. 4a and 4b show examples of controls allowing a user to select a subset of information elements in accordance with specific examples of implementation of the invention.

In FIG. 4a, the control is in the form of a pull-down menu having an actuator button 300 that, when actuated, is operative for displaying or concealing a list of available additional information elements. The selected information elements are shown with a check mark (✓) next to the information elements. The unselected information elements are shown without a check mark (✓) next to the information elements. The pull-down menu further includes a sliding bar 302 for allowing additional information elements to be listed.

Figure 4B:
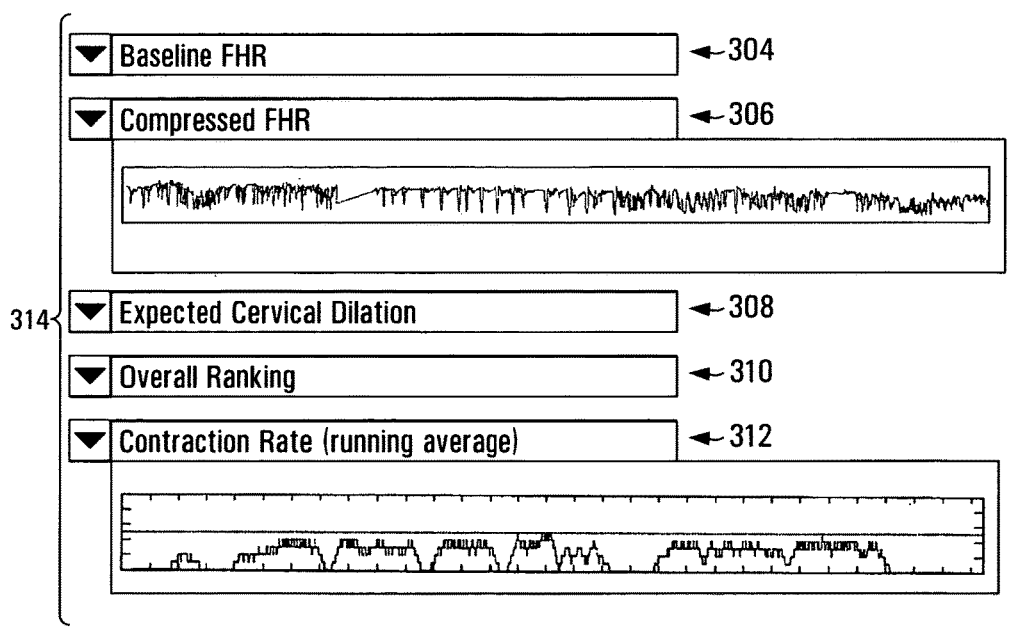

In FIG. 4b, an alternative example of a set of controls 314 including controls 304 306 308 310 and 312 is depicted. Each control in the set of controls 314 is associated to a respective information element and allows a user to select the associated viewing window to be displayed or concealed. In the example depicted, the controls 304 306 308 310 and 312 are pull-down windows positioned one over the other with the time axis, when applicable, of each of the windows are aligned. The actuation of a given control causes the associated viewing window to be displayed (when the window had previously been concealed) or concealed (when the window had previously been displayed). It will be appreciated that the unselected windows may either be fully concealed (i.e. not displayed in any way) on the user interface or alternatively may be partially concealed without detracting from the spirit of the invention.

In yet another embodiment, not shown in the figures, the set of possible viewing windows includes one or more groupings of viewing windows including at least two viewing windows. The user interface includes a control allowing the user to select a grouping viewing windows such as to allow the user to select two (2) or more viewing windows simultaneously. Preferably, the groupings of viewing windows are configured such that a given grouping includes viewing windows pertaining to related feature measurements or to feature measurements that should be considered as a group in order to provide useful to the clinical staff. For example, a grouping for a mother in pre-term labour could be provided, the grouping including viewing windows for displaying the contraction count, the tocolytic medication level and the fetal heart rate. The grouping for a mother in pre-term labour may omit cervical dilation and station. Alternatively, a grouping for a mother in term labour could be provided, the display including a grouping having viewing windows for displaying station and dilation. The grouping for a mother in term labour would likely omit tocolytic medication levels.

It is to be appreciated that the examples described are non-exhaustive and that such examples are provided for the purpose of illustration only. Suitable types of controls other than the ones described above may be used without detracting from the spirit of the invention.

Second Example

Figure 3B:
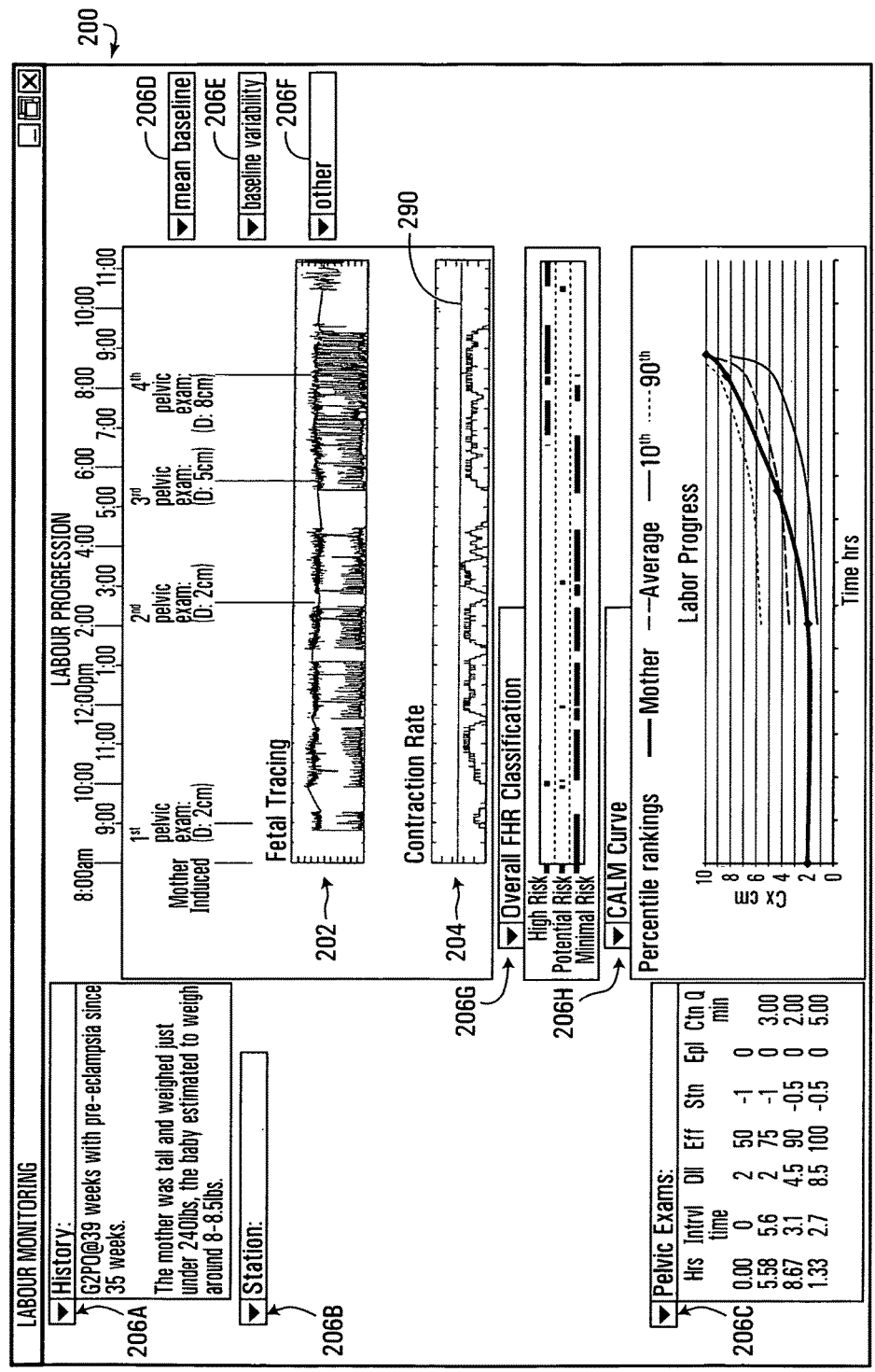
FIG. 3b shows a specific example of implementation of a graphical user interface implemented by the system shown in FIG. 1 for providing labour related information in accordance with a second non-limiting example of implementation of the invention.

With reference to FIG. 3b, a second specific example of a graphical user interface module 200 implemented by graphical user interface module generator 262 (shown in FIG. 2) is shown. The graphical user interface module 200, similar to that depicted in FIG. 3a, includes a first viewing window 202 and a second viewing window 204. In the first viewing window 202, a first tracing indicative of a fetal heart rate signal is displayed and in the second viewing window 204, a second tracing indicative of a uterine contraction pattern associated with the obstetrics patient is displayed. The graphical user interface module also includes a set of controls 206a-h for allowing a user to select for display additional viewing windows from a set of possible viewing windows. As described above, the additional viewing windows in the set of additional viewing windows are adapted for conveying various information related to the assessment of labour progression for the obstetrics patient. Such information was derived by the analysis toolkit module 260 (shown in FIG. 2). The graphical user interface module displays the selected subset of additional viewing windows simultaneously with the first viewing window 202 and second viewing window 204.

In the specific implementation depicted in FIG. 3b, the second tracing in the second viewing window 204 conveys a running average of a uterine contraction count associated with the obstetrics patient. The second viewing window 204 also includes a third tracing 290 indicative of a threshold uterine contraction count.

In the example depicted in FIG. 3b, the graphical user interface module is depicted as including a set of controls 206a-h each of which, when actuated, displays or conceals an associated additional viewing window. Each control 206a-h is associated to respective information elements. In the example shown, the additional viewing windows associated to controls 206a, 206b, 206c, 206g and 206h are displayed simultaneously with the first viewing window 202 and second viewing window 204. The additional viewing windows corresponding to un-selected information elements and associated to controls 206d, 206e and 206f are not displayed on the graphical user interface.

In the example depicted in FIG. 3b, an additional viewing window is displayed conveying information related to levels of risk associated with labour. This additional viewing window is associated with control 206g. More specifically, the additional viewing window displays over a time segment data conveying levels of risk associated with labour. In the example shown in FIG. 3b, the time segment is divided into a plurality of sub-segments and data conveying a respective level of risk associated with labour for an obstetrics patient is depicted for each sub-segment.

In the example depicted in FIG. 3b, an additional viewing window is displayed conveying information related to the expected dilation of the cervix over time. This additional viewing window is associated with control 206h. More specifically, the additional viewing window displays over a time the expected dilation of the cervix. This information is derived by the corresponding tool in the analysis toolkit module 260.

Although the controls 206a-h depicted in FIG. 3b are shown in association with a set of additional viewing windows that can be displayed or concealed, it will be appreciated that the control may be of any suitable form for allowing the user to select a subset of a set of additional viewing windows. For example, the control may be comprised of text boxes, drop down menus, handles, images (eg. icons) or any other suitable means on the user interface. The user may provide his selection through the user input device 118 which may be any one or a combination of the following: keyboard, pointing device, touch sensitive surface or speech recognition unit.

In a variant, the graphical user interface module displays one or more additional viewing windows on the basis of a user profile. In a specific implementation, graphical user interface module makes use of a user identifier obtained, for example, during a log-in process, to determine a subset of viewing windows to be displayed for a given user. The set of viewing windows to be displayed for a given user may be specified in a "user preferences" database whereby user identifiers are mapped to a set of identifiers corresponding to respective subsets of viewing windows. Advantageously, this allows users to have a preferred subset of viewing windows that are displayed when using the interface. Suitable functionality for allowing the user to configure and or modify the entries in the user preferences database may be provided. Manners in which to implement such functionality is well-known the art of software design and the specific manner in which the configuration and modification functionality is provided is not critical to the invention and as such will not be described further here.

In yet another variant, the graphical user interface module is adapted for enabling a user to select a profile from a group of possible profiles, at least some profiles being associated to two (2) or more viewing windows. Suitable functionality for allowing the user to configure and or modify the profiles in the group of possible profiles may also be provided. Manners in which to implement such functionality is well-known the art of software design and the specific manner in which the configuration and modification functionality is provided is not critical to the invention and as such will not be described further here.

Third Example

Figure 3C:
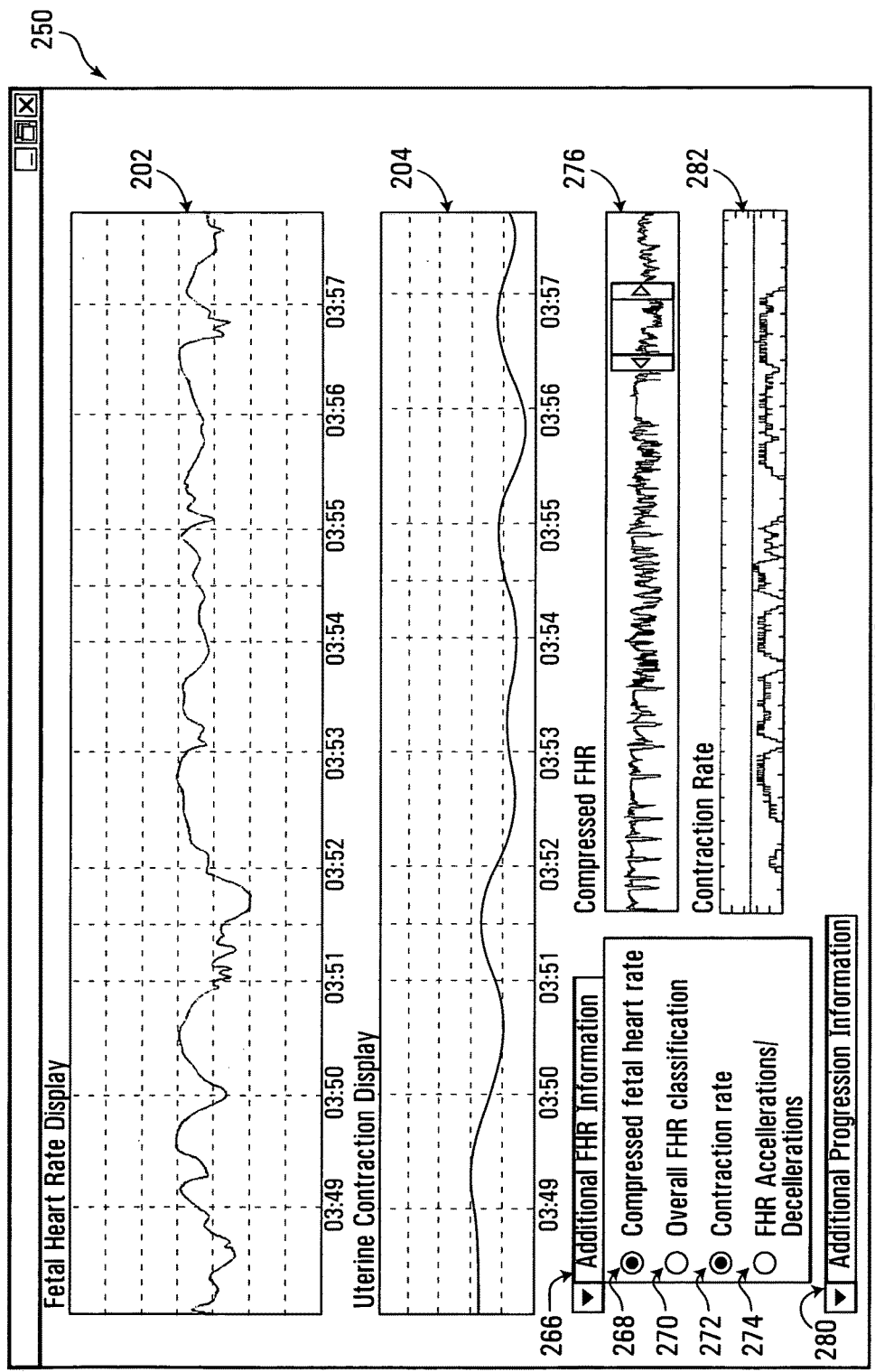
FIG. 3c shows a specific example of implementation of a graphical user interface implemented by the system shown in FIG. 1 for providing labour related information in accordance with a third non-limiting example of implementation of the invention.

With reference to FIG. 3c, a second specific example of a graphical user interface module 250 implemented by graphical user interface module generator 262 (shown in FIG. 2) is shown. As in the case of the graphical user interface module 200 of FIGS. 3a and 3b, the graphical user interface module 250 includes a first viewing window 202 and a second viewing window 204. In the first viewing window 202, a first tracing indicative of a fetal heart rate signal is displayed and in the second viewing window 204, a second tracing indicative of a uterine contraction pattern associated with the obstetrics patient is displayed. The graphical user interface module also includes a control 266 for allowing a user to select additional viewing windows for display from a set of possible viewing windows. As described above, the additional viewing windows in the set of possible viewing windows are adapted for conveying various information elements related to the assessment of labour progression for the obstetrics patient. Such information elements were derived by the analysis toolkit module 260 (shown in FIG. 2). The user may provide his selection through the user input device 118 which may be any one or a combination of the following: keyboard, pointing device, touch sensitive surface or speech recognition unit. The graphical user interface module displays the selected subset of additional viewing windows simultaneously with the first viewing window 202 and second viewing window 204.

In FIG. 3c, the control 266 is in the form of a pull-down menu. The pull down menu includes a plurality of selection buttons 268 270 272 274 associated to respective information elements, each of the selection buttons 268 270 272 274 being adapted to be actuated or de-actuated to either select or un-select the associated information element. In the example shown, selection buttons 268 and 272 are actuated to select respective associated information elements "Compressed fetal heart rate" and "Contraction rate". As shown, additional viewing windows 276 282 corresponding to selected information elements "Compressed fetal heart rate" and "Contraction rate" are displayed simultaneously with the first viewing window 202 and second viewing window 204. The additional viewing windows corresponding to un-selected information elements, namely "Overall FHR classification" and "FHR accelerations/decelerations" are not displayed on the graphical user interface.

In a specific example of implementation, the additional viewing windows are combined into several sets of additional viewing windows. The combination may be effected on the basis of any suitable logical/heuristic rules. In a specific example of implementation, of the type depicted in FIG. 3c, the additional viewing windows are combined into a first set conveying information data elements derived from a fetal heart rate signal and a second set conveying information data elements derived at least in part on the basis of clinical measurements obtained from the obstetrics patient. Optionally, each set of additional viewing windows is associated with a respective control, namely controls 266 and 280. Control 280 is displayed on the graphical user interface for allowing a user to select a subset of the second set of additional viewing windows. The selected subset of the second set of additional viewing windows is then displayed simultaneously with the first viewing window and second viewing window.

Additional Viewing Windows

As indicated above, the graphical user interface module includes a control for allowing a user to select additional viewing windows from a set of additional viewing windows. The viewing windows in the set of possible viewing windows are adapted for conveying various additional information elements related to the assessment of labour progression for the obstetrics patient. The specific type of information elements to be displayed by the graphical user interface module in the possible viewing windows will vary from one implementation to the other and will depend on the functionality implemented by the toolkit module 260 (shown in FIG. 2).

Certain additional viewing window in the set of possible viewing windows are adapted to convey information elements derived at least in part on the basis of the fetal heart rate signal. Such information elements are typically derived by processing the fetal heart rate and may include, without being limited to:

1) fetal heart rate feature measurements such as:
   mean baseline;
   mean baseline variability;
   decelerations;
   accelerations;
2) fetal heart rate classification;
3) others . . . .

In a specific example of implementation, the fetal heart rate feature measurements may be represented as tracings of the fetal heart rate feature measurements over time or in numerical format (text format) indicating the values of the feature measurements over time.

In accordance with a specific implementation, in addition to the fetal heart rate measurements, information element indicating a safety limit for a feature measurement related to labor progression is also displayed. The information element indicating a safety limit for a feature measurement may include, for example, a threshold value associated to the fetal heart rate feature measurement. In a specific example, each the information element includes one or more threshold values associated to the corresponding fetal heart rate feature measurement. The one or more threshold values may be depicted graphically as tracings or in numerical format (text format).

In a specific example of implementation, threshold values are depicted by dotted lines positioned on the graphs at levels corresponding to the threshold values for the various feature measurements. The threshold values mark a boundary between feature measurements (or rankings) considered having a lower level of risk and feature measurements (or rankings) considered having a higher level of risk. It will be readily apparent that multiple thresholds may be used for marking boundaries between different levels of risk (eg. low, intermediate, high etc. . . . ). The number of threshold levels for a given feature measurement will typically depend on the type of feature element measurement. The manner in which the threshold levels are selected and well as the number of threshold levels is not critical to the invention and as such will not be described further here.

In a specific example of implementation, the graphical user interface module is adapted for displaying a visual indicator in association with a viewing window in the set of additional viewing windows, the visual indicator conveying that a fetal heart rate feature measurement has exceeded an associated safety limit. For example, the visual indicator may be used to draw the attention of the clinical staff to a feature measurement that has exceeded a threshold and that is now consider to be associated to a high level of risk. For example, in cases where the additional viewing window associated with the fetal heart rate feature measurement that has exceeded its associated threshold value is fully or partially displayed, the visual indicator may be displayed in conjunction with that additional viewing window. Any suitable type of visual indicator may be used to draw attention to the additional viewing window. Examples of visual indicators that may be used include, without being limited to

- Variations in color. For example, a color scheme may be established whereby certain colors are associated with varying levels of risk. Portions of the window may turn a certain color associated with a high level of risk when the fetal heart rate feature measurement exceeds an associated threshold value. A non-limiting example of a color scheme is green=normal; yellow: intermediate risk level; red: high level of risk however any suitable color scheme may be used;
- Variation in display intensity of the additional viewing window. For example, flashing or blinking of the additional viewing window may be used as a visual indicator to draw attention;
- Variation in the size of the size or position of the additional viewing window. For example, the appearance of the additional viewing window may be made to appear more prominently on the user interface or at a location that is more likely to draw the attention of the clinical staff.
- Displaying a message prompting/alerting the clinical staff to observe what is going on in the additional viewing window.

Optionally, in cases where the additional viewing window associated with the fetal heart rate feature measurement that has exceeded its associated threshold value is not at least partially displayed, the graphical user interface module is adapted to cause the additional viewing window to be displayed without the intervention of the user. A visual indicator may then (optionally) also be displayed in conjunction with that additional viewing window.

It will readily be appreciated that the list of functionality and additional viewing windows is non-exhaustive and has been provided for the purpose of illustration only.

Specific Physical Implementation

Those skilled in the art should appreciate that in some embodiments of the invention, all or part of the functionality previously described herein with respect to the apparatus implementing a user interface for displaying labour related information may be implemented as pre-programmed hardware or firmware elements (e.g., application specific integrated circuits (ASICs), electrically erasable programmable read-only memories (EEPROMs), etc.), or other related components.

In other embodiments of the invention, all or part of the functionality previously described herein with respect to the apparatus for implementing a graphical user interface module for displaying labour related information may be implemented as software consisting of a series of instructions for execution by a computing unit. The series of instructions could be stored on a medium which is fixed, tangible and readable directly by the computing unit, (e.g., removable diskette, CD-ROM, ROM, PROM, EPROM or fixed disk), or the instructions could be stored remotely but transmittable to the computing unit via a modem or other interface device (e.g., a communications adapter) connected to a network over a transmission medium. The transmission medium may be either a tangible medium (e.g., optical or analog communications lines) or a medium implemented using wireless techniques (e.g., microwave, infrared or other transmission schemes).

Figure 5:
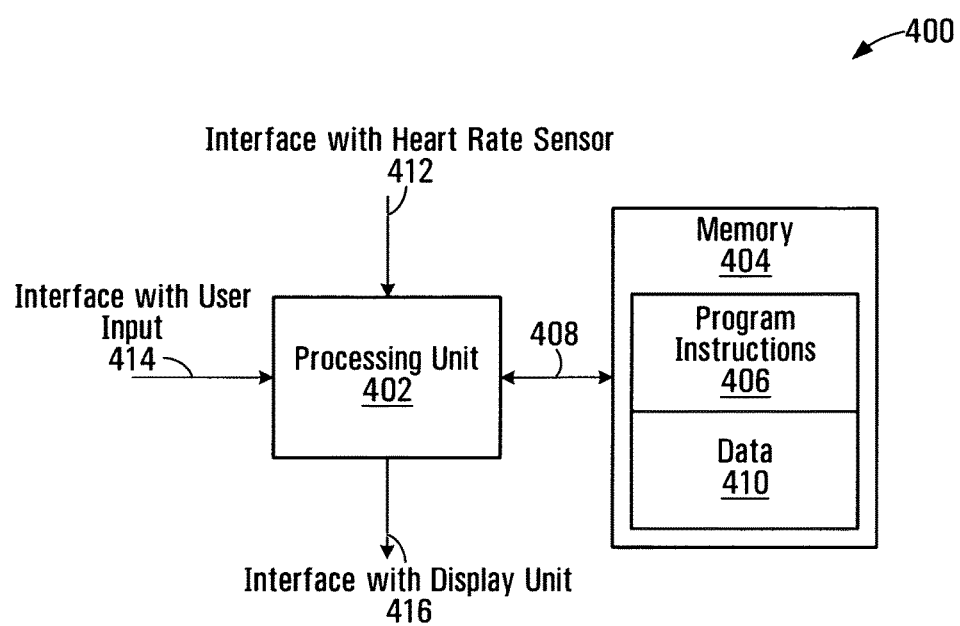
FIG. 5 is a block diagram of an apparatus for providing labour related information in accordance with a specific example of implementation of the present invention.

The apparatus implementing a user interface for displaying labour related information may be configured as a computing unit of the type depicted in FIG. 5, including a processing unit 402 and a memory 404 connected by a communication bus 408. The memory 404 includes data 410 and program instructions 406. The processing unit 402 is adapted to process the data 410 and the program instructions 406 in order to implement the functional blocks described in the specification and depicted in the drawings. In a non-limiting implementation, the program instructions 406 implement the functionality of processing unit 106 described above. The computing unit 400 may also comprise a number of interfaces 412 414 416 for receiving or sending data elements to external devices. For example, interface 412 is used for receiving data streams indicative of a fetal heart rate signal and interface 414 is used for receiving a control signal from the user indicating the subset of labour related information data to be displayed. Interface 416 is for releasing a signal causing a display unit to display the user interface generated by the program instructions 406.

Figure 7:
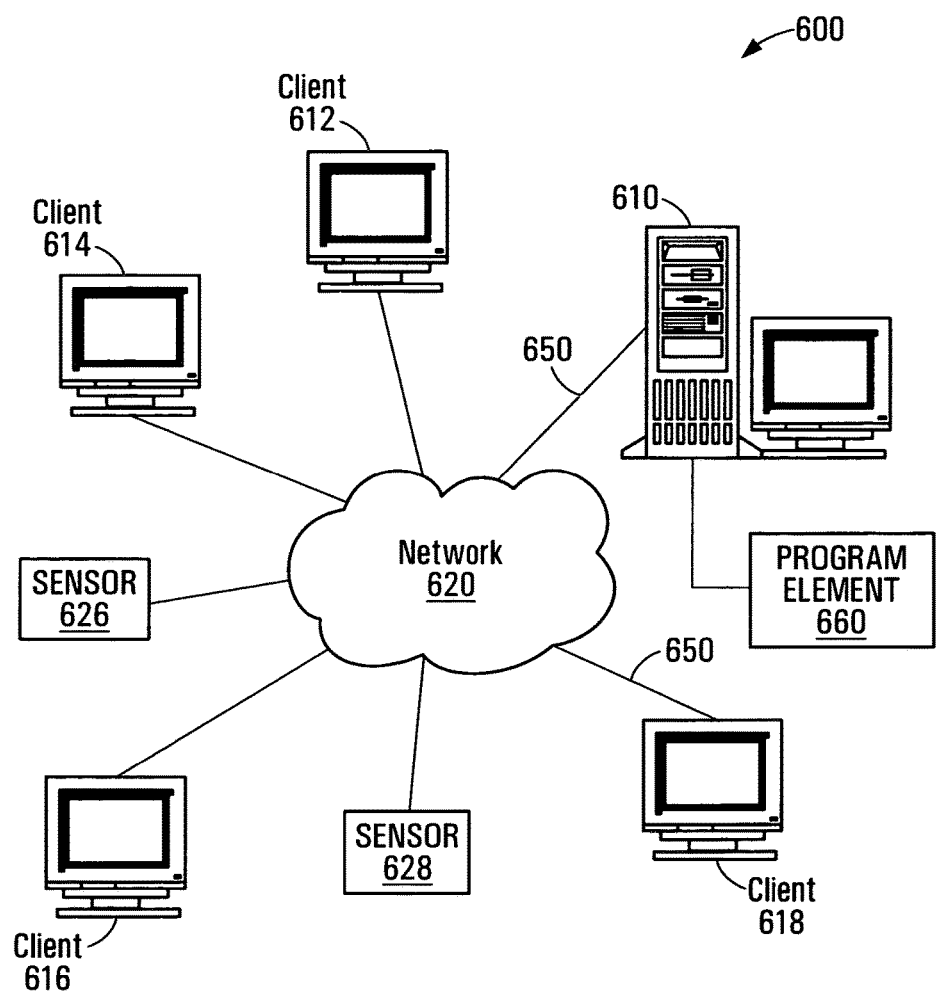
FIG. 7 shows a functional block diagram of a client-server system for providing labour related information in accordance in accordance with an alternative specific non-limiting example of implementation of the present invention.

It will be appreciated that the system for implementing a user interface for displaying labour related information may also be of a distributed nature where the data is collected at one location and transmitted over a network to a server unit implementing the graphical user interface. The server unit may then transmit a signal for causing a display unit to display the graphical user interface. The display unit may be located in the same location as the data was collected, in the same location as the server unit or in yet another location. FIG. 7 illustrates a network-based client-server system 600 for displaying heart rate information. The client-server system 600 includes a plurality of client systems 612 614 616 618 connected to a server system 610 through network 620. The communication links 650 between the client systems 612 614 616 618 and the server system 610 can be metallic conductors, optical fibers or wireless, without departing from the spirit of the invention. The network 620 may be any suitable network including but not limited to a global public network such as the Intranet, a private network and a wireless network. The server 610 may be adapted to process and issue signals to display multiple heart rate signals originating from multiple sensors 626 628 concurrently using suitable methods known in the computer related arts.

Figure 6:
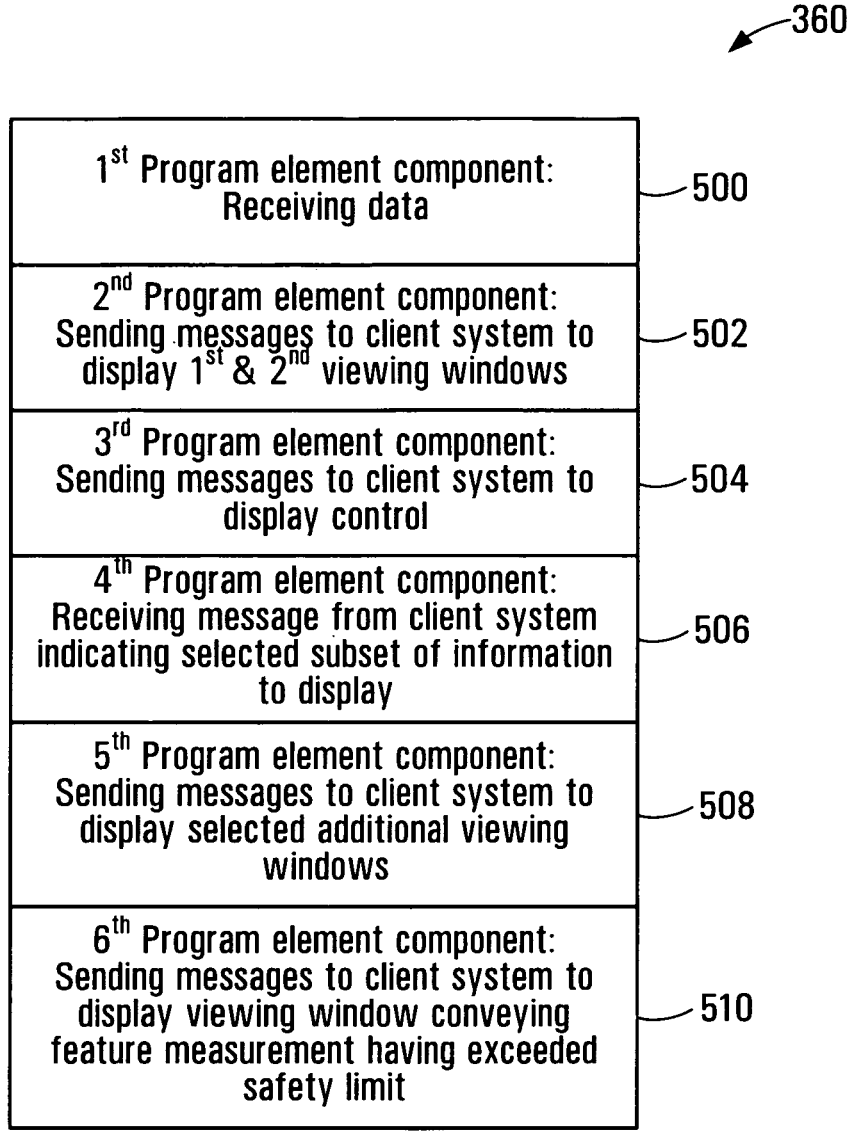
FIG. 6 is a high level conceptual block diagram of a program element for implementing a graphical user interfaces of the type shown in FIGS. 3a, 3b and 3c in accordance with a specific example of implementation of the present invention.

The server system 610 includes a program element 660 for execution by a CPU. Program element 660 implements similar functionality as program instructions 406 (shown in FIG. 5) and includes the necessary networking functionality to allow the server system 610 to communicate with the client systems 612 614 616 618 over network 620. In a non-limiting implementation, program element 660 includes a number of program element components, each program element components implementing a respective portion of the functionality of the user interface for displaying heart rate information. FIG. 6 shows a non-limiting example of the architecture of program element 660 at the server system. As shown, the program element 660 includes six program element components:

1. the first program element component 500 is executed on server system 610 and is for receiving signals conveying labour information;
2. the second program element component 502 is executed on server system 610 and is for sending messages to a client system, say client system 614, for causing client system 614 to displaying a first viewing window selected from a set of possible viewing windows, each viewing window in the set of possible viewing windows conveying a feature measurement related to labour progression, at least one viewing window in the set of possible viewing windows conveying:
    i) a given feature measurement; and
    ii) a safety limit associated to the given feature measurement;
3. the third program element component 504 is executed on server system 610 and is for sending messages to client system 614 for causing client system 614 to display a control allowing a user to select a subset of the set of possible viewing windows;
4. the fourth program element component 506 is executed on server system 610 and is for receiving a message from client system 614 indicative of a selected subset of viewing windows;
5. the fifth program element component 508 is executed on server system 610 and is for sending messages to client system 614 for causing client system 614 to display, simultaneously with the first viewing window, the selected subset of additional viewing windows;
6. the fifth program element component 508 is executed on server system 610 and is for sending messages to client system 614 for causing client system 614 to display, simultaneously with the first viewing window, a viewing window conveying a given feature measurement in response to the given feature measurement exceeding the associated safety limit associated to the given feature measurement.

Those skilled in the art should further appreciate that the program instructions may be written in a number of programming languages for use with many computer architectures or operating systems. For example, some embodiments may be implemented in a procedural programming language (e.g., "C") or an object oriented programming language (e.g., "C++" or "JAVA").

Although the present invention has been described in considerable detail with reference to certain preferred embodiments thereof, variations and refinements are possible without departing from the spirit of the invention. Therefore, the scope of the invention should be limited only by the appended claims and their equivalents.

The invention claimed is:

1. A system for monitoring labour progression for an obstetrics patient, said system comprising:
    a) a fetal heart rate sensor for generating signals conveying fetal heart rate information;
    b) a uterine activity sensor for generating signals conveying maternal contraction information;
    c) a processor arrangement in communication with said fetal heart rate sensor and said uterine activity sensor for receiving the signals conveying the fetal heart rate information and the maternal contraction information, said processor arrangement including at least one processor and a non-transitory storage medium containing instructions for execution by the at least one processor, the instructions when executed by the at least one processor being configured for:
        i) directing the processor arrangement to implement a Graphical User Interface (GUI) providing a first viewing window displaying measurements over time of a first feature characterizing labour progression of the obstetrics patient, the measurements of the first feature being derived by processing at least one of the fetal heart rate information and the maternal contraction information;
        ii) said GUI being configured for presenting an input object configured to accept one or more user selections identifying one or more additional features characterizing the labour progression of the obstetrics patient selected from a set of additional selectable features;
        iii) directing the processor arrangement to process at least one of the fetal heart rate information and the maternal contraction information to:
            (1) derive measurements over time associated with a specific additional feature not presented in a viewing window displayed on the GUI, the specific additional feature characterizing the labour progression of the obstetrics patient in the set of additional selectable features, the measurements over time associated with the specific additional feature conveying risk levels over time associated with the labour progression of the obstetrics patient;
            (2) process the risk levels conveyed by the derived measurements of the specific additional feature and a risk level safety limit corresponding to the specific additional feature to detect excesses associated with the specific additional feature characterizing the labour progression;
        iv) selectively causing one or more alarm events at least in part in response to detection of the excesses, said one or more alarm events including dynamically adapting the GUI without human intervention, the dynamically adapting the GUI causing the GUI to present dynamic adaptations to:
  (1) deliver additional information to the user by displaying an additional viewing window for displaying the measurements over time of the specific additional feature, wherein the GUI is configured to display the additional viewing window concurrently with the first viewing window and wherein the GUI is configured to display the measurements of the first feature and the measurements of the specific additional feature in a substantially time aligned manner to allow the user to view over concurrent time periods the measurements of the first feature and the measurements associated with the specific additional feature conveying risk levels associated with the labour progression of the obstetrics patient; and
  (2) present a visual indicator in connection with the displayed additional viewing window to alert the user to the excesses detected in connection with the derived measurements of the specific additional feature characterizing the labour progression of the obstetrics patient;
d) a display device in communication with said processor arrangement for presenting the GUI to the user.

2. A system as defined in claim 1, wherein said one or more alarm events include triggering the generation of an audio signal in connection with the displayed additional viewing window to alert the user to the excesses detected in connection with the derived measurements of the specific additional feature characterizing the labour progression of the obstetrics patient.

3. A system as defined in claim 1, wherein:
a) the GUI is configured to receive through the input object a specific user selection identifying a specific user-selected additional feature from the set of additional selectable features;
b) in response to receipt of the user selection identifying the specific user-selected additional feature, adapting the GUI to deliver additional information by displaying an other additional viewing window for displaying measurements over time of the specific user-selected additional feature, wherein the GUI is configured to display the other additional viewing window concurrently with the first viewing window and wherein the GUI is configured to display the measurements of the first feature and the measurements of the specific user-selected additional feature in a substantially time aligned manner to allow the user to view over concurrent time periods the measurements of the first feature and the measurements associated with the specific user-selected additional feature.

4. A system as defined in claim 1, wherein the GUI is configured to receive a signal conveying a user identifier associated with the user of the system, the user identifier being associated with a user profile stored on a computer readable medium accessible by the at least one processor, and wherein the instructions when executed by the at least one processor are configured for:
a) adapting the GUI to deliver additional information by displaying an other additional viewing window for displaying measurements over time of a user-specific additional feature, the user-specific additional feature being derived based on the user identifier received by the GUI and the user profile stored on the computer readable medium, wherein the GUI is configured to display the other additional viewing window concurrently with the first viewing window and wherein the GUI is configured to display the measurements of the first feature and the measurements of the user-specific additional feature in a substantially time aligned manner to allow the user to view over concurrent time periods the measurements of the first feature and the measurements associated with the user-specific additional feature.

5. A system as defined in claim 1, wherein said system includes an input for receiving signals conveying clinical measurements associated with the obstetrics patient, the measurements derived over time associated with the specific additional feature characterizing the labour progression of the obstetrics patient being derived at least in part by processing the clinical measurements associated with the obstetrics patient and at least one of the fetal heart rate information and the maternal contraction information.

6. A system as defined in claim 5, wherein the clinical measurements associated with the obstetrics patient include cervical dilation measurements taken over time.

7. A system as defined in claim 5, wherein the clinical measurements associated with the obstetrics patient include level of descent measurements taken over time.

8. A system as defined in claim 1, wherein the first viewing window conveys a tracing conveying a uterine contraction pattern over time, the uterine contraction pattern being derived at least in part by processing the maternal contraction information.

9. A system as defined in claim 1, wherein the input object includes a selection box presenting the user with a listing conveying the set of additional selectable features.

10. A system as defined in claim 1, wherein the input object allows the user to provide one or more user selections by using an input device selected from the set consisting of a mouse, keyboard, pointing device, speech recognition unit and touch sensitive screen.

11. A method for monitoring labour progression for an obstetrics patient, said method comprising:
a) receiving signals from a fetal heart rate sensor conveying fetal heart rate information;
b) receiving signals from a uterine activity sensor conveying maternal contraction information;
c) providing a processor arrangement including at least one processor and a non-transitory storage medium containing instructions for execution by the at least one processor, the instructions when executed by the at least one processor being configured for:
  i) directing the processor arrangement to implement a Graphical User Interface (GUI) providing a first viewing window displaying measurements over time of a first feature characterizing labour progression of the obstetrics patient, the measurements of the first feature being derived by processing at least one of the fetal heart rate information and the maternal contraction information;
  ii) said GUI being configured for presenting an input object configured to accept one or more user selections identifying one or more additional features characterizing the labour progression of the obstetrics patient selected from a set of additional selectable features;
  iii) directing the processor arrangement to process at least one of the fetal heart rate information and the maternal contraction information to:
    (1) derive measurements over time associated with a specific additional feature not presented in a viewing window displayed on the GUI, the specific additional feature characterizing the labour progression of the obstetrics patient in the set of additional selectable features, the measurements over time associated with the specific additional feature conveying risk levels over time associated with the labour progression of the obstetrics patient;

(2) process the risk levels conveyed by the derived measurements of the specific additional feature and a risk level safety limit corresponding to the specific additional feature to detect excesses associated with the specific additional feature characterizing the labour progression;

iv) selectively causing one or more alarm events at least in part in response to detection of the excesses, said one or more alarm events including dynamically adapting the GUI without human intervention, the dynamically adapting the GUI causing the GUI to present dynamic adaptations to:

(1) deliver additional information to the user by displaying an additional viewing window for displaying the measurements over time of the specific additional feature, wherein the GUI is configured to display the additional viewing window concurrently with the first viewing window and wherein the GUI is configured to display the measurements of the first feature and the measurements of the specific additional feature in a substantially time aligned manner to allow the user to view over concurrent time periods the measurements of the first feature and the measurements associated with the specific additional feature conveying risk levels associated with the labour progression of the obstetrics patient;

(2) present a visual indicator in connection with the displayed additional viewing window to alert the user to the excesses detected in connection with the derived measurements of the specific additional feature characterizing the labour progression of the obstetrics patient;

d) using a display device in communication with said processor arrangement for presenting the GUI to the user.

12. A method as defined in claim 11, wherein said one or more alarm events include triggering the generation of an audio signal in connection with the displayed additional viewing window to alert the user to the excesses detected in connection with the derived measurements of the specific additional feature characterizing the labour progression of the obstetrics patient.

13. A method as defined in claim 11, wherein:
a) the GUI is configured to receive through the input object a specific user selection identifying a specific user-selected additional feature from the set of additional selectable features;
b) in response to receipt of the user selection identifying the specific user-selected additional feature, adapting the GUI to deliver additional information by displaying an other additional viewing window for displaying measurements over time of the specific user-selected additional feature, wherein the GUI is configured to display the other additional viewing window concurrently with the first viewing window and wherein the GUI is configured to display the measurements of the first feature and the measurements of the specific user-selected additional feature in a substantially time aligned manner to allow the user to view over concurrent time periods the measurements of the first feature and the measurements associated with the specific user-selected additional feature.

14. A method as defined in claim 11, wherein the GUI is configured to receive a signal conveying a user identifier associated with the user of the system, the user identifier being associated with a user profile stored on a computer readable medium accessible by the at least one processor, and wherein the instructions when executed by the at least one processor are configured for:
a) adapting the GUI to deliver additional information by displaying an other additional viewing window for displaying measurements over time of a user-specific additional feature, the user-specific additional feature being derived based on the user identifier received by the GUI and the user profile stored on the computer readable medium, wherein the GUI is configured to display the other additional viewing window concurrently with the first viewing window and wherein the GUI is configured to display the measurements of the first feature and the measurements of the user-specific additional feature in a substantially time aligned manner to allow the user to view over concurrent time periods the measurements of the first feature and the measurements associated with the user-specific additional feature.

15. A method as defined in claim 11, wherein the instructions when executed by the at least one processor are further configured for receiving signals conveying clinical measurements associated with the obstetrics patient, the measurements derived over time associated with the specific additional feature characterizing the labour progression of the obstetrics patient being derived at least in part by processing the clinical measurements associated with the obstetrics patient and at least one of the fetal heart rate information and the maternal contraction information.

16. A method as defined in claim 15, wherein the clinical measurements associated with the obstetrics patient include cervical dilation measurements taken over time.

17. A method as defined in claim 15, wherein the clinical measurements associated with the obstetrics patient include level of descent measurements taken over time.

18. A method as defined in claim 11, wherein the first viewing window conveys a tracing conveying a uterine contraction pattern over time, the uterine contraction pattern being derived at least in part by processing the maternal contraction information.

19. A method as defined in claim 11, wherein the input object includes a selection box presenting the user with a listing conveying the set of additional selectable features.

20. A method as defined in claim 11, wherein the input object allows the user to provide one or more user selections by using an input device selected from the set consisting of a mouse, keyboard, pointing device, speech recognition unit and touch sensitive screen.

21. A computer program product including computer executable instructions stored on a non-transitory computer readable medium, said computer program product implementing a system for monitoring labour progression for an obstetrics patient, said instructions when executed by a processor arrangement being configured for:
a) receiving signals from a fetal heart rate sensor, said signals conveying fetal heart rate information;
b) receiving signals from a uterine activity sensor, said signals conveying maternal contraction information;

c) directing the processor arrangement to implement a Graphical User Interface (GUI) providing a first viewing window displaying measurements over time of a first feature characterizing labour progression of the obstetrics patient, the measurements of the first feature being derived by processing at least one of the fetal heart rate information and the maternal contraction information, said GUI being configured for presenting an input object configured to accept one or more user selections identifying one or more additional features characterizing the labour progression of the obstetrics patient selected from a set of additional selectable features;

d) directing the processor arrangement to process at least one of the fetal heart rate information and the maternal contraction information to:
  (1) derive measurements over time associated with a specific additional feature not presented in a viewing window displayed on the GUI, the specific additional feature characterizing the labour progression of the obstetrics patient in the set of additional selectable features, the measurements over time associated with the specific additional feature conveying risk levels over time associated with the labour progression of the obstetrics patient;
  (2) process the risk levels conveyed by the derived measurements of the specific additional feature and a risk level safety limit corresponding to the specific additional feature to detect excesses associated with the specific additional feature characterizing the labour progression;

e) selectively causing one or more alarm events at least in part in response to detection of the excesses, said one or more alarm events including dynamically adapting the GUI without human intervention, the dynamically adapting the GUI causing the GUI to present dynamic adaptations to:
  i) deliver additional information to the user by displaying an additional viewing window for displaying the measurements over time of the specific additional feature, wherein the GUI is configured to display the additional viewing window concurrently with the first viewing window and wherein the GUI is configured to display the measurements of the first feature and the measurements of the specific additional feature in a substantially time aligned manner to allow the user to view over concurrent time periods the measurements of the first feature and the measurements associated with the specific additional feature conveying risk levels associated with the labour progression of the obstetrics patient;
  ii) present a visual indicator in connection with the displayed additional viewing window to alert the user to the excesses detected in connection with the derived measurements of the specific additional feature characterizing the labour progression of the obstetrics patient;

f) presenting the GUI to the user using a display device in communication with said processor arrangement.

22. A computer program product as defined in claim 21, wherein said one or more alarm events include triggering the generation of an audio signal in connection with the displayed additional viewing window to alert the user to the excesses detected in connection with the derived measurements of the specific additional feature characterizing the labour progression of the obstetrics patient.

23. A computer program product as defined in claim 21, wherein:
  a) the GUI is configured to receive through the input object a specific user selection identifying a specific user-selected additional feature from the set of additional selectable features;
  b) in response to receipt of the user selection identifying the specific user-selected additional feature, adapting the GUI to deliver additional information by displaying an other additional viewing window for displaying measurements over time of the specific user-selected additional feature, wherein the GUI is configured to display the other additional viewing window concurrently with the first viewing window and wherein the GUI is configured to display the measurements of the first feature and the measurements of the specific user-selected additional feature in a substantially time aligned manner to allow the user to view over concurrent time periods the measurements of the first feature and the measurements associated with the specific user-selected additional feature.

24. A computer program product as defined in claim 21, wherein the GUI is configured to receive a signal conveying a user identifier associated with the user of the system, the user identifier being associated with a user profile stored on a computer readable medium accessible by the processor arrangement, and wherein the instructions when executed by the processor arrangement are configured for:
  a) adapting the GUI to deliver additional information by displaying an other additional viewing window for displaying measurements over time of a user-specific additional feature, the user-specific additional feature being derived based on the user identifier received by the GUI and the user profile stored on the computer readable medium, wherein the GUI is configured to display the other additional viewing window concurrently with the first viewing window and wherein the GUI is configured to display the measurements of the first feature and the measurements of the user-specific additional feature in a substantially time aligned manner to allow the user to view over concurrent time periods the measurements of the first feature and the measurements associated with the user-specific additional feature.

25. A computer program product as defined in claim 21, wherein the instructions when executed by the processor arrangement are further configured for receiving signals conveying clinical measurements associated with the obstetrics patient, the measurements derived over time associated with the specific additional feature characterizing the labour progression of the obstetrics patient being derived at least in part by processing the clinical measurements associated with the obstetrics patient and at least one of the fetal heart rate information and the maternal contraction information.

26. A computer program product as defined in claim 25, wherein the clinical measurements associated with the obstetrics patient include cervical dilation measurements taken over time.

27. A computer program product as defined in claim 26, wherein the clinical measurements associated with the obstetrics patient include level of descent measurements taken over time.

28. A computer program product as defined in claim 21, wherein the first viewing window conveys a tracing conveying a uterine contraction pattern over time, the uterine contraction pattern being derived at least in part by processing the maternal contraction information.

29. A computer program product as defined in claim 21, wherein the input object includes a selection box presenting the user with a listing conveying the set of additional selectable features.

30. A computer program product as defined in claim 21, wherein the input object allows the user to provide one or more user selections by using an input device selected from the set consisting of a mouse, keyboard, pointing device, speech recognition unit and touch sensitive screen.

\* \* \* \* \*